United States Patent [19]
Ondetti

[11] 3,973,006
[45] Aug. 3, 1976

[54] PEPTIDE ENZYME INHIBITORS OF ANGIOTENSIN I

[75] Inventor: Miguel Angel Ondetti, Princeton, N.J.

[73] Assignee: E. R. Squibb & Sons, Inc., Princeton, N.J.

[22] Filed: Feb. 21, 1975

[21] Appl. No.: 551,888

[52] U.S. Cl. .......................... 424/177; 260/112.5 R
[51] Int. Cl.² ................ A61K 37/00; C07C 103/52
[58] Field of Search ............... 260/112.5 R; 424/177

[56] References Cited
UNITED STATES PATENTS

| | | | |
|---|---|---|---|
| 3,819,486 | 6/1974 | Murao et al. ................ | 260/112.5 R |
| 3,832,337 | 8/1974 | Ondetti et al. ............... | 260/112.5 R |
| 3,862,114 | 1/1975 | Scardrett ..................... | 260/112.5 R |
| 3,867,364 | 2/1975 | Umezawa et al. ............ | 260/112.5 R |
| 3,878,185 | 4/1975 | Murao et al. ................ | 260/112.5 R |

OTHER PUBLICATIONS
Cushman et al.: Experientia, 29, 1032–1035 (1973).

Primary Examiner—Lewis Gotts
Assistant Examiner—Reginald J. Suyat
Attorney, Agent, or Firm—Lawrence S. Levinson; Merle J. Smith; Burton Rodney

[57] ABSTRACT

Ester and amides of the nonapeptide Pyr-Trp-Pro-Arg-Pro-Gln-Ile-Pro-Pro have been found to inhibit the hypertensive effect of angiotensin I.

6 Claims, No Drawings

PEPTIDE ENZYME INHIBITORS OF ANGIOTENSIN I

BACKGROUND OF THE INVENTION

The action of the enzyme renin on renin substrate, a pseudoglobulin in blood plasma, produces a polypeptide angiotensin I, also known as hypertensin I. The latter is converted by an enzyme to angiotensin II, also known as hypertensin II or angiotonin. Angiotensin II is an active pressor substance which is present in the plasma of individuals with hypertension in quantities sufficient to maintain elevated blood pressure. Inhibition of the enzyme responsible for the conversion of angiotensin I to angiotensin II serves to remove a cause of essential hypertension.

U.S. Pat. No. 3,832,337 to Ondetti et al. discloses various peptides and acylated peptides which inhibit enzymatic conversion of angiotensin I into angiotensin II, among such peptides being Pyr-Trp-Pro-Arg-Gln-Ile-Pro-Pro.

Studies on structure-activity relationships concerning peptides as disclosed in U.S. Pat. No. 3,832,337 indicated that a free terminal carboxyl group is needed to obtain potent inhibitors in vitro and in vivo. For example, see the paper by Cushman et al., "Inhibition of Angiotensin-Converting Enzyme by Analogs of Peptides from Bothrops jararaca Venom", Experienta 29, 1032 (1973), Birkhauser Verlag, Basel, Switzerland. However, it has now been found that not only is the above nonapeptide an inhibitor of angiotensin I induced hypertension, but esters and amides of such nonapeptide are useful for such purpose as well. This is surprising inasmuch as such esters and amides show very low or no detectable enzyme inhibition activity in vitro. Generally, in vitro activity of peptides in this area usually corresponds to in vivo activity thereof. Accordingly, it is indeed unexpected that such esters and amides are potent inhibitors of angiotensin I induced hypertension.

OBJECTS OF THE INVENTION

It is, accordingly, an object of the present invention to provide compounds which inhibit the conversion of angiotensin I into angiotensin II in vivo and thereby antagonize the hypertensive effect of angiotensin I. Another object is to provide compounds which are effective in relieving hypertension. A further object is to provide a method for alleviating hypertension. These and other objects of the present invention will be apparent from the following description.

DETAILED DESCRIPTION

Unless otherwise indicated in the following specification and claims, all amino acids are of the L-configuration.

In describing the peptides of the present invention, the following abbreviations will be used throughout the specification and claims:

Arg - arginine
Gln - glutamine
Ile - isoleucine
Pro - proline
Pyr - pyroglutamic acid
Trp - tryptophane The following peptides of the present invention have been found to be effective in inhibiting angiotensin I induced hypertension:

Pyr-Trp-Pro-Arg-Pro-Gln-Ile-Pro-Pro-OR      I wherein R is alkyl

Pyr-Trp-Pro-Arg-Pro-Gln-Ile-Pro-Pro-NH$_2$      II

The alkyl group of the above ester may comprise a straight or branched chain hydrocarbon fragment containing 1 to 10 carbons, and preferably 1 to 6 carbons, such as methyl, ethyl, propyl, isopropyl, n-butyl, s-butyl, t-butyl, pentyl, hexyl, heptyl, octyl, nonyl and decyl, as well as the various isomers of the latter six groups.

The esters of

Pyr-Trp-Pro-Arg-Pro-Gln-Ile-Pro-Pro,      III such as the methyl and t-butyl esters, are particularly preferred.

The esters of the invention are preferably prepared by reaction of a di-, tri-, tetra-, penta-, hexa-, hepta- or octa-peptide including a Pro- terminal group protected by an alkyl ester with one or more peptides, as is necessary, employing conventional peptide preparatory techniques, to form the nonapeptide alkyl ester (I) of the invention. In this manner, the ester of the invention may be formed directly without having to first form the parent compound Pyr-Trp-Pro-Arg-Pro-Gln-Ile-Pro-Pro.      III However, it will be appreciated that the esters as well as the amide of the invention may be formed by first forming the parent peptide I in accordance with the procedures as outlined in U.S. Pat. No. 3,832,337 the disclosure of which is incorporated herein by reference and thereafter adding the alkyl ester or amide group to the terminal Pro employing conventional procedures.

The compounds of the present invention are capable of inhibiting the hypertensive effect of angiotensin I when administered to mammals such as rats, mice, or dogs, in a dosage level of from about 0.5 to about 10 mg./kg. For the latter purpose they may be administered parenterally by incorporating the appropriate dosage with a physiologically-acceptable carrier.

The following examples illustrate the present invention without, however, limiting the same thereto. All temperatures are expressed in degrees Centigrade.

EXAMPLE 1

Benzyloxycarbonyl-isoleucyl-proline-proline

Prolyl-proline hydrobromide (4.24 g) is dissolved in a mixture of dimethylformamide (40 ml) and triethylamine (2.8 ml). Benzyloxycarbonyl-isoleucine p-nitrophenyl ester (9.27 g) and 1-hydroxybenzotriazole (3 g) are added and the mixture is stored at room temperature for 16 hours. Dimethylaminopropylamine (1 ml) is added and after 2 hours the solvent is removed in vacuo. The residue is dissolved in ethyl acetate (200 ml) and washed sequentially with 0.1 N hydrochloric acid, and water. The organic phase is dried over magnesium sulfate and concentrated to dryness in vacuo to yield 13.8 g solid. This material is applied to a silica gel column (300 g) in ethyl acetate and eluted with the same solvent. The fractions containing the desired above-titled tripeptide are pooled and concentrated to dryness.

EXAMPLE 2

Methyl benzyloxycarbonyl-isoleucyl-prolyl-prolinate

The tripeptide acid of Example 1 (4.6 g) is dissolved in methanol and treated with an ethereal solution of diazomethane until a persistent yellow color is obtained. After 0.5 hour a few drops of acetic acid are added to discharge the yellow color; the solvent is removed in vacuo and replaced with ethyl acetate. This solution is washed sequentially with 0.1 N HCl, water, saturated sodium bicarbonate and water. The organic phase is dried over magnesium sulfate and concentrated to dryness to yield the title compound.

EXAMPLE 3

Methyl benzyloxycarbonyl-glutaminyl-isoleucyl-prolyl-prolinate

The tripeptide of Example 2 (1.4 g) is dissolved in 95° ethanol (30 ml) and N hydrochloric acid (3 ml.) Palladium on charcoal (0.3 g) is added and the suspension is stirred under a positive hydrogen pressure until no more carbon dioxide is detected in the outcoming gases. The catalyst is removed by filtration and the filtrate is concentrated to dryness in vacuo. The residue is dissolved in a mixture of dimethylformamide (6 ml) and triethylamine (0.5 ml). Benzyloxycarbonyl-glutamine p-nitrophenyl ester (1.6 g) and 1-hydroxybenzotriazole (0.5 g) are added and the reaction is allowed to proceed at room temperature until the ninhydrin test is negative. Dimethylaminopropylamine (0.5 ml) is added and the reaction is allowed to proceed for another hour. Ethyl acetate (200 ml) is added and the ensuing solution is washed neutral. The organic phase is dried over magnesium sulfate and the solvent is removed in vacuo to yield the title compound.

EXAMPLE 4

Methyl benzyloxycarbonyl-ω-nitroarginyl-prolyl-glutaminyl-isoleucyl-prolyl-prolinate The tetrapeptide of Example 3 (14 g) is dissolved in absolute ethanol (325 ml) and N hydrochloric acid (23 ml). Palladium on charcoal (3.0 g) is added and the mixture is stirred under positive hydrogen pressure until no more carbon dioxide is liberated. The catalyst is filtered off and the filtrate is concentrated to dryness. The residue is dissolved in dimethylformamide (43 ml) and triethylamine (3.2 ml). Benzyloxycarbonyl nitroarginyl-proline 2,4,5-trichlorophenyl ester (15.7 g) and 1-hydroxybenzotriazole (3.1 g) are added immediately and the reaction is allowed to proceed until the ninhydrin test is negative. Dimethylamino propylamine (5.4 ml) is added and after two hours the solvent is removed in vacuo. The residue is dissolved in ethyl acetate and the solution is washed neutral. The ethyl acetate is concentrated in vacuo to ca 70 ml and the solution poured into 1 liter of vigorously stirred ether. The precipitate is filtered and dried to give the title compound.

EXAMPLE 5

Methyl benzyloxycarbonyl-tryptophyl-prolyl-arginyl-prolyl-glutaminyl-isoleucyl-prolyl-prolinate The hexapeptide of Example 4 (1.8 g) is dissolved in absolute ethanol (27 ml) and N hydrochloric acid (4 ml). Palladium on charcoal (0.38 g) is added and the mixture is stirred under a positive hydrogen pressure until the ultraviolet absorption of the nitroguanidine chromophore can no longer be detected. The catalyst is filtered off and the filtrate is concentrated to dryness in vacuo. The residue is dissolved in dimethylformamide (10 ml) and triethylamine (0.28 ml). Benzyloxycarbonyl-tryptophyl-proline 2,4,5-trichlorophenyl ester (1.5 g) and 1-hydroxybenzotriazole (0.3 g) are added immediately and the reaction is allowed to proceed until the ninhydrin test is negative. The triethylamine hydrochloride precipitate is filtered off and the precipitate is poured into 250 ml of vigorously stirred ethyl acetate. The precipitate is filtered and dried to give the title compound.

EXAMPLE 6

Pyroglutamyl-tryptophyl-prolyl-arginyl-prolyl-glutaminyl-isoleucyl-prolyl-proline, methyl ester The octapeptide of Example 5 (10 g) is dissolved in absolute ethanol (150 ml) and N hydrochloric acid (9 ml). Palladium on charcoal (2 g) is added and the suspension is stirred under positive hydrogen pressure until no more carbon dioxide is evolved. The catalyst is removed by filtration and the filtrate is concentrated to dryness in vacuo. The residue is dissolved in dimethylformamide (40 ml) and 1-hydroxybenzotriazole (1.2 g), triethylamine (1.2 ml) and pyroglutamic acid 2,4,5-trichlorophenyl ester are added in rapid succession. The reaction is allowed to proceed until the ninhydrin test is negative. The triethylamine hydrochloride precipitate is removed by filtration and the filtrate is poured into 1.1 liters of vigorously stirred ethyl acetate. The precipitate is filtered and dried to give the title compound. This material can be purified by chromatography on Sephadex G-25 in 0.01 M ammonium bicarbonate.

EXAMPLE 7 n-Butyl benzyloxycarbonyl-isoleucyl-proline-prolinate

A solution of benzyloxycarbonyl-isoleucyl-prolyl-proline (4.5 g) in chloroform (30 ml) is added slowly to a solution of 1-n-butyl-3-p-tolyltriazene (1.9 g) in chloroform (15 ml). When the reaction is complete the chloroform solution is washed neutral and the organic phase is dried over magnesium sulfate and concentrated to dryness in vacuo to give the title compound.

EXAMPLE 8 n-Butyl-benzyloxycarbonyl-glutaminyl-isoleucyl-prolyl-prolinate

This compound is prepared by the procedure of Example 3, starting with the tripeptide in Example 7.

EXAMPLE 9 n-Butyl benzyloxycarbonyl-ω-nitroarginyl-prolyl-glutaminyl-isoleucyl-prolyl-prolinate This compound is prepared by the procedure of Example 4, starting with the tetrapeptide obtained in Example 8.

Example 10 n-Butyl benzyloxycarbonyl-tryptophyl-propyl-arginyl-prolyl-glutaminyl-isoleucyl-prolyl-prolinate This compound is prepared by the procedure of Example 5, starting with the hexapeptide of Example 9.

EXAMPLE 11

Pyroglutamyl-tryptophyl-prolyl-arginyl-prolyl-glutaminyl-isoleucyl-prolyl-proline, n-butyl ester This compound is prepared by the procedure of Example 6, starting with the octapeptide of Example 10.

EXAMPLE 12

Benzyloxycarbonyl-isoleucyl-prolyl-proline amide

Benzyloxycarbonyl-isoleucyl-prolyl-proline (4.5 g) is dissolved in a mixture of tetrahydrofuran (30 ml) and triethylamine (1.4 ml). The solution is chilled in a −5° cooling bath and isobutyl chloroformate (1.6 ml) is added. The solution is allowed to warm to room temperature (10 minutes) and concentrated aqueous ammonia (10 ml) is added. After four hours stirring at room temperature, the reaction is concentrated in vacuo, diluted with ethyl acetate and washed sequentially with saturated sodium bicarbonate, water, 0.1 N hydrochloric acid and water. The organic phase is dried over magnesium sulfate and concentrated to dryness in vacuo to give the title compound.

EXAMPLE 13

Benzyloxycarbonyl-glutaminyl-isoleucyl-prolyl-proline amide

This compound is prepared by the procedure of Example 3, starting with the tripeptide of Example 12.

EXAMPLE 14

Benzyloxycarbonyl-ω-nitroarginyl-prolyl-glutaminyl-isoleucyl-prolyl-proline amide This compound is prepared by the procedure of Example 4, starting with the tetrapeptide of Example 13.

EXAMPLE 15

Benzyloxycarbonyl-tryptophyl-prolyl-arginyl-prolyl-glutaminyl-isoleucyl-prolyl-proline amide This compound is prepared by the procedure of Example 5, starting with the hexapeptide of Example 14.

EXAMPLE 16

Pyroglutamyl-tryptophyl-prolyl-arginyl-prolyl-glutaminyl-isoleucyl-proline amide This compound is prepared by the procedure of Example 6, starting with the octapeptide of Example 15.

Example 17

Benzyloxycarbonyl-tryptophyl-prolyl-arginyl-prolyl-glutaminyl-isoleucyl-prolyl-proline, tert-butyl ester t-Butyl benzyloxycarbonyl nitroarginyl-proline-glutaminyl-isoleucyl-proline-prolinate (9.42 g, ~10 mmoles) is dissolved in 135 ml absolute ethanol and 20 ml N HCl and 1.9 g 10% palladium on carbon with stirring under positive hydrogen pressure for 22 hours. It is filtered through hyflo and taken to dryness in vacuo. The crude residue is dissolved in 50 ml of dimethylformamide and 1.4 ml triethylamine followed immediately by (12 mmoles) 7.4 g of benzyloxycarbonyl-tryptophyl-prolyl-2,4,5-trichlorophenyl ester. Over a 30 hour period an additional 1.5 mmoles of benzyloxycarbonyl-tryptophyl-prolyl-2,4,5-trichlorophenyl ester and 1.5 mmoles of triethylamine are added. After 50 hours the triethylamine.HCl is filtered and the filtrate added to 1.2 l of vigorously swirling ethyl acetate. The precipitate is filtered and washed with ethyl acetate to give the title compound. Yield - 10.64 g.

EXAMPLE 18

Pyroglutamyl-tryptophyl-prolyl-arginyl-prolyl-glutaminyl isoleucy-prolyl-proline, t-butyl ester 10 g (~8.5 mmoles) of the peptide of Example 17 is dissolved in 150 ml of absolute ethanol and 8.5 ml N HCl and 2 g of 10% palladium on carbon and stirred under positive hydrogen pressure for eight hours. It is filtered through hyflo and the filtrate concentrated to dryness in vacuo to yield 9.2 g of crude residue.

The crude residue is dissolved in 40 ml of dimethylformamide and 1.14 g (8.5 mmoles) of 1-hydroxy benzotriazole and (8.5 mmoles) 1.2 ml of triethylamine followed immediately by 3.14 g pyroglutamic acid 2,4,5-trichlorophenyl ester (20% excess). An additional 0.6 ml triethylamine is added. The reaction is allowed to run overnight. The triethylamine.HCl is filtered and the filtrate poured into 1.1 l of vigorously swirling ethyl acetate. The recovered precipitate is filtered through paper No. 42 and washed with ethyl acetate to yield 9.0 g of the title compound.

Purification is achieved on a DEAE Sephadex A-25 column by elution with 0.005 M $NH_4HCO_3$.

EXAMPLE 19

Pyroglutamyl-tryptophyl-prolyl-arginyl-prolyl-glutaminyl-isoleucyl-prolyl-proline, methyl ester Pyroglutamyl-tryptophyl-prolyl-arginyl-prolyl-glutaminyl-isoleucyl-prolyl-proline (1.6 g) is dissolved in 80 ml of methanol. To this, excess ethereal diazomethane is added and the solution is kept for 7 hours at room temperature. Acetic acid is added to destroy the excess diazomethane and the resulting mixture is concentrated to dryness in vacuo.

Purification is effected on a Sephadex G-25 column eluting with 0.01 M $(NH_4)HCO_3$, following by a DEAE Sephadex A-25 column eluting with 0.005 M $NH_4HCO_3$ to yield 1.1 g of the title compound.

EXAMPLE 20

Pyroglutamyl-tryptophyl-prolyl-arginyl-prolyl-glutaminyl-isoleucyl-prolyl-prolinamide Pyroglutamyl-tryptophyl-prolyl-arginyl-pyrolyl-glutaminyl-isoleucyl-prolyl-proline (1 g) is dissolved in 6 ml of dimethyl sulfoxide with gentle warming. The solution is cooled to room temperature and 0.14 ml of triethylamine and 0.16 ml of isobutyl chloroformate are added. The reaction mixture is stirred for 15 minutes. One ml of concentrated ammonium hydroxide is added and the reaction proceeds for four hours prior to slow addition to 200 ml of vigorously swirling ethyl acetate. A precipitate is formed which is filtered and washed with ethyl acetate to yield 1.375 g of solids.

This material is purified on a 225 ml column of DEAE Sephadex A-25 by elution with 0.005 M NH$_4$HCO$_3$ to yield 924 mg of the title compound.

EXAMPLE 21

For determination of I$_{50}$ values (concentration of peptide expressed in micrograms/ml. producing a 50% inhibition of angiotensin-converting enzyme), varying concentrations of the peptide of Example 19 are added to 13 × 100 mm. assay tubes containing a final volume of 0.25 ml. containing 100 mM. potassium phosphate buffer, pH 7.5, 30 mM. NaCl, and 0.3 mM. angiotensin I. Enzymatic reactions are initiated by addition of enzyme and incubation is carried out at 37°. The concentration of the peptide of Example 19 of the present invention which inhibits conversion of 50% of angiotensin I into angiotensin II is found to be 7 μg./ml as opposed to an I$_{50}$ (μg/ml) of 0.9 for the parent peptide Pyr-Trp-Pro-Arg-Pro-Gln-Ile-Pro-Pro. This in vitro test clearly demonstrates that the Example 19 peptide of the invention is substantially less potent than the parent control peptide in vitro in inhibiting conversion of angiotensin I into angiotensin II.

EXAMPLE 22

The peptide of Example 19 and the parent Control peptide Pyr-Trp-Pro-Arg-Pro-Gln-Ile-Pro-Pro are administered intravenously in two atropinized anesthetized male rats infused with pentolinium followed by an injection of 0.10 μg/kg of angiotensin I. On the basis of the degree of inhibition of angiotensin I induced pressor response, it is found that the in vivo activity of the Example 19 peptide of the invention is roughly equivalent to that of the parent Control peptide.

What is claimed is:

1. A peptide having the formula

Pyr-Trp-Pro-Arg-Pro-Gln-Ile-Pro-Pro-OR or

Pyr-Trp-Pro-Arg-Pro-Gln-Ile-Pro-Pro-NH$_2$ wherein R is an alkyl group containing 1 to 10 carbons.

2. The peptide as defined in claim 1 wherein R is an alkyl group containing 1 to 6 carbons.

3. The peptide as defined in claim 2 wherein R is methyl.

4. The peptide as defined in claim 2 wherein R is t-butyl.

5. A method for treating hypertension in mammalian species, which comprises administering a therapeutic amount of a peptide as defined in claim 1.

6. A method for forming the peptide as defined in claim 1 and having the formula Pyr-Trp-Pro-Arg-Pro-Gln-Ile-Pro-Pro-OR,   (1)

which comprises deprotecting a peptide of the formula

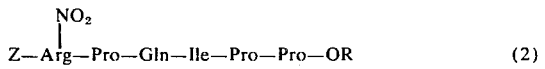

wherein Z is benzyloxycarbonyl, and then reacting the deprotected peptide with a peptide of the formula Z-Trp-Pro-Tcp   (3)

wherein Z is as defined above and Tcp is 2,4,5-trichlorophenyl ester to form a peptide of the formula Z-Trp-Pro-Arg-Pro-Gln-Ile-Pro-Pro-OR wherein Z is as defined above, and reacting the latter peptide (4) after deprotection with Pyr-OTcp   (4)

wherein Tcp is as defined above, to form the peptide of formula (1).

* * * * *

UNITED STATES PATENT AND TRADEMARK OFFICE
CERTIFICATE OF CORRECTION

PATENT NO. : 3,973,006
DATED : August 3, 1976
INVENTOR(S) : Miguel Angel Ondetti It is certified that error appears in the above-identified patent and that said Letters Patent are hereby corrected as shown below:

Column 1, line 22, "Ilc" should read --Ile--.

Column 5, line 66, after "isoleucyl" insert -- -prolyl--.

Column 6, line 26, "isoleucy" should read --isoleucyl--.
Column 6, line 66, "pyrolyl" should read --prolyl--.

Signed and Sealed this

Twenty-sixth Day of October 1976

[SEAL]

Attest:

RUTH C. MASON
*Attesting Officer*

C. MARSHALL DANN
*Commissioner of Patents and Trademarks*